United States Patent [19]
Brown et al.

[11] Patent Number: 5,292,320
[45] Date of Patent: Mar. 8, 1994

[54] RADIAL MEDICAL LASER DELIVERY DEVICE

[75] Inventors: Joseph Brown, Acworth, Ga.; Wolfgang Neuberger, Monchen-Gladbach, Fed. Rep. of Germany

[73] Assignee: CeramOptec, Inc., Enfield, Conn.

[21] Appl. No.: 908,382

[22] Filed: Jul. 6, 1992

[51] Int. Cl.⁵ ............................................. A61M 29/02
[52] U.S. Cl. ....................................... 606/15; 606/17; 606/14
[58] Field of Search ............................ 128/395–398, 128/6, 7; 604/20, 21; 606/12–16, 27, 28

[56] References Cited
U.S. PATENT DOCUMENTS

| | | | |
|---|---|---|---|
| 4,641,912 | 2/1987 | Goldenberg | 606/10 |
| 4,648,892 | 3/1987 | Kittrell et la. | 606/12 |
| 4,740,047 | 4/1988 | Abe et al. | 606/16 |
| 4,800,886 | 1/1989 | Nestor | 128/634 |
| 4,822,335 | 4/1989 | Kawai et al. | 604/20 |
| 4,848,323 | 7/1989 | Marijnissen et al. | 128/6 |
| 4,955,377 | 9/1990 | Lennox et al. | 606/27 |
| 4,994,060 | 2/1991 | Rink et al. | 606/15 |
| 5,019,075 | 5/1991 | Spears et al. | 606/28 |
| 5,037,172 | 8/1991 | Hekman et al. | 385/31 |
| 5,057,099 | 10/1991 | Rink . | |

*Primary Examiner*—Stephen C. Pellegrino
*Assistant Examiner*—Mike Peffley
*Attorney, Agent, or Firm*—Kenneth P. Glynn

[57] ABSTRACT

The present invention involves a medical delivery system capable of emitting radiation with wavelengths between 190 nm and 16 um in one or more essentially directed, predetermined patterns. It includes at least one solid optical fiber, having a core and a cladding on the core. The cladding has a refractive index smaller than the core, having an input end suitably configured to connect to an appropriate radiation source and having a distal end in the proximity of which two or more grooves are penetrating into the core. The gooves have at least partial reflector capability so as to deflect radiation thereto radially in one or more predetermined patterns. The invention also includes methods of performing medical procedures utilizing the aforesaid device.

11 Claims, 5 Drawing Sheets

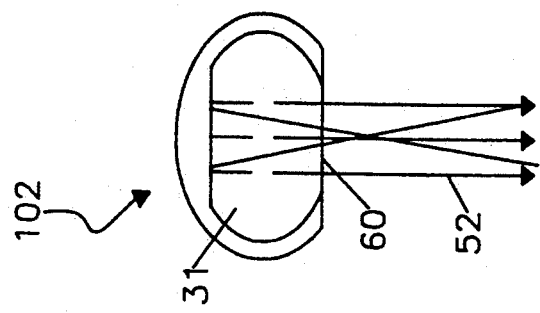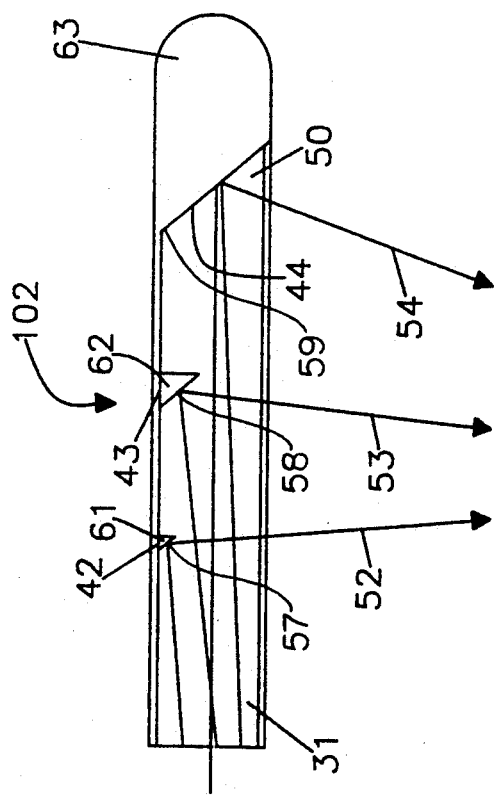

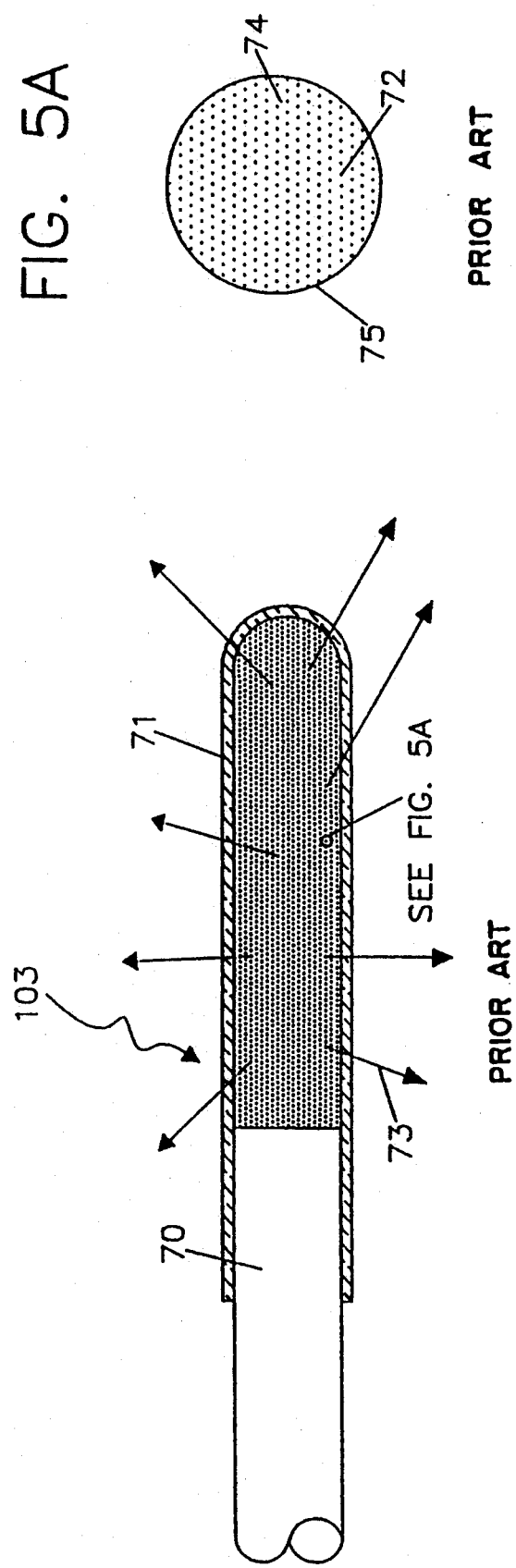

RADIAL MEDICAL LASER DELIVERY DEVICE

BACKGROUND OF THE INVENTION

1. Field of the Invention

This invention relates to a laser delivery device, and more particularly to such delivery devices that emit radiation radially from the distal end of an optical fiber.

2. Prior Art Statement

Technological change in laser delivery devices is rapidly taking place in the laser medical field with the onset of minimally invasive procedures such as laser laparoscopy. The laparoscopist, a physician or surgeon who performs laparascopies, is often challenged with positioning the delivery device, i.e., the optical fiber(s), at angles radially to the laparoscope axis in order to irradiate the target perpendicularly. However, in many cases moving a laparoscope radially is very difficult or is impossible. As an alternative, the laparoscope, which is normally rigid, may have an adjustable fiber deflector called a bridge. The bridge may be adjusted at the proximal end causing radial movements to the distal end of the fibers. This adjustment is, however, limited by the bend radius of the fibers and/or the bridge device and cannot offer full capabilities. Therefore, techniques to emit radiation radially from the distal end of the fiber without bending are needed.

Reflecting tips secured on the distal fiber end, such as metal caps incorporating a mirror surface at a 45° angle relative to the fiber axis are state of the art and have been used successfully in procedures such as lithotripsy with high pulse powered (Q-switched) Yttrium Aluminum Garnet Lasers.

For many surgical procedures requiring an even illumination (such as prostate treatment or photodynamic therapy) the point source-like radiation pattern from this known device is ill suited.

The state of the art devices used in photodynamic therapy incorporate a glue, i.e. epoxy, containing cap with scattering medium dispersed in it. These caps can produce a relatively homogeneous radial pattern. However, the output is diffuse and they are somewhat limited in power handling capability due to the limitations of the glue.

In summary, the present state of the art for radial laser radiation delivery is restricted to either point sources (size of the source comparable to the fiber cross section) or to essentially diffuse radiators with limited power handling capabilities. U.S. Pat. No. 4,740,047 describes a point source type of device using a cut fiber with a reflective surface to deflect a beam for lateral application.

While methods to control the fiber tip temperature aimed at preventing damage to the distal tip of the laser delivery device have been described in U.S. Pat. No. 5,057,099 no control method has been described to prevent or limit damage to the tissue itself that seems applicable to treatments such as laser prostatectomy. Thus, while this recently issued patent allows for temperature control to optimize particular surgical or medical procedures, it does not address or satisfactorily resolve the need for proper lateral and radial delivery of laser beams to satisfy varied needs for varied procedures.

Thus, the prior art neither teaches nor renders obvious the present invention device set forth herein.

SUMMARY OF THE INVENTION

Described is a device capable of delivering high laser power at selected angles or any angle essentially radially to the axis of an optical fiber. The fiber emits the laser radiation from a wider area at the distal end in a well directed, essentially non-diffuse pattern with a plurality of reflective surfaces, having different angles or sizes, within the fiber itself.

Surgical procedures, such as transurethral laser prostatectomy, are beneficially performed using preferred embodiments of the device. The device may comprise feedback control mechanisms from the tissue to regulate radiation delivery dosimetry with procedural requirements.

BRIEF DESCRIPTION OF THE DRAWINGS

The invention, together with further objects, advantages, aspects and features thereof, will be more clearly understood from the following description taken in connection with the accompanying drawings:

FIG. 3 is a detailed view of FIG. 2 showing reflective metal coating used for deflection;

FIG. 4 is a cross section of FIG. 3;

FIG. 5 and FIG. 5A show a conventional state of the art Photo Dynamic Therapy delivery device;

DESCRIPTION OF THE PREFERRED EMBODIMENTS

It is an object of this invention to provide a new and improved radial laser delivery device to overcome the disadvantages of prior radial laser delivery devices, such as power handling capability, area of coverage, extent of coverage, radially directedness of radiation from an extended source, etc. By "radial" and "radially" are meant extending outwardly from the central axis of a fiber and not parallel thereto. In this application, they are meant to include extending outwardly at right angles as well as at any other angles and to include full circumference and only partial circumference radiation.

Another object of this invention is to describe a control mechanism and an improved device method to carry out treatments such as laser prostatectomy and photodynamic therapy.

Figure 1:
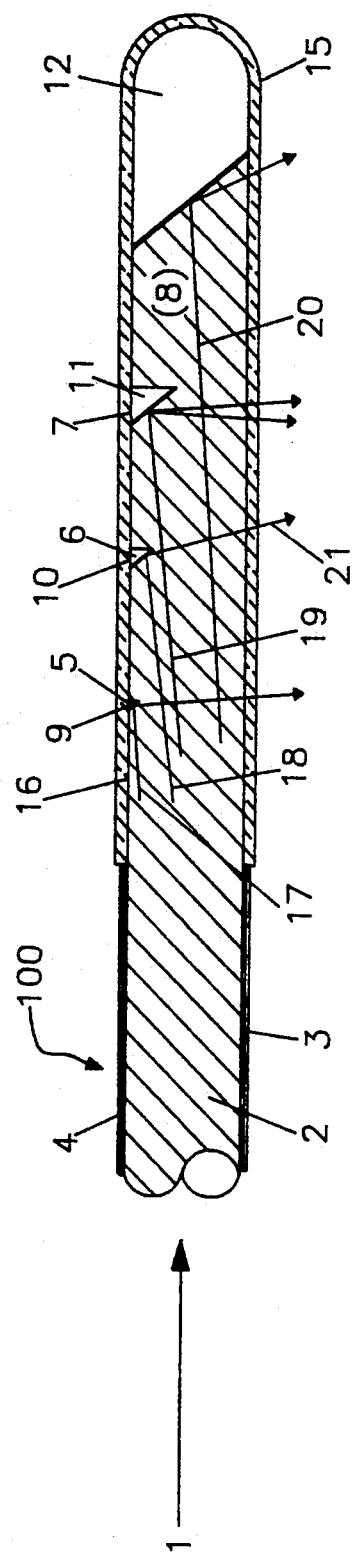
FIG. 1 is a side view of a radial medical radiation delivery device using air pockets created by the core and a transparent cap for total reflection.

FIG. 1 illustrates a side view of present invention device 100, a typical preferred embodiment of the invention, at its distal end. The optical fiber 1 has a core 2, a cladding 3 and one or more protective coating layers 4. Core 2 is grooved on one side, and grooves 5, 6 and 7 are of increasing size and/or angles, as shown. Core 2 distal end 8 is encapsulated with a protective, transparent cap 15 over a predetermined length so as to cover all the grooves 5, 6 and 7; this resulting in a series of air pockets 9, 10, 11 and 12. The cap can be affixed to the fiber by any medically safe glue 16. If the inclination of the fronts of the grooves (facing incoming radiation)

measured from the most inclined ray 17, 18 and 19 travelling in the fiber 1 is chosen such that it is lower than the angle of the total reflection limit between the optical fiber core and air, all rays coming through the fiber from the proximal end (input end of the radiation source, or laser) will be totally reflected and thus exit in radial direction as shown by the typical arrows such as arrow 21.

By progressively increasing the depth of each groove towards the distal end 8 of the fiber 1, more and more radiation is diverted from the axial path into the radial direction resulting in the desired extended directed radiation. This creates a defined, predetermined area of radiation application that is much greater than a reflected point source.

Figure 2:
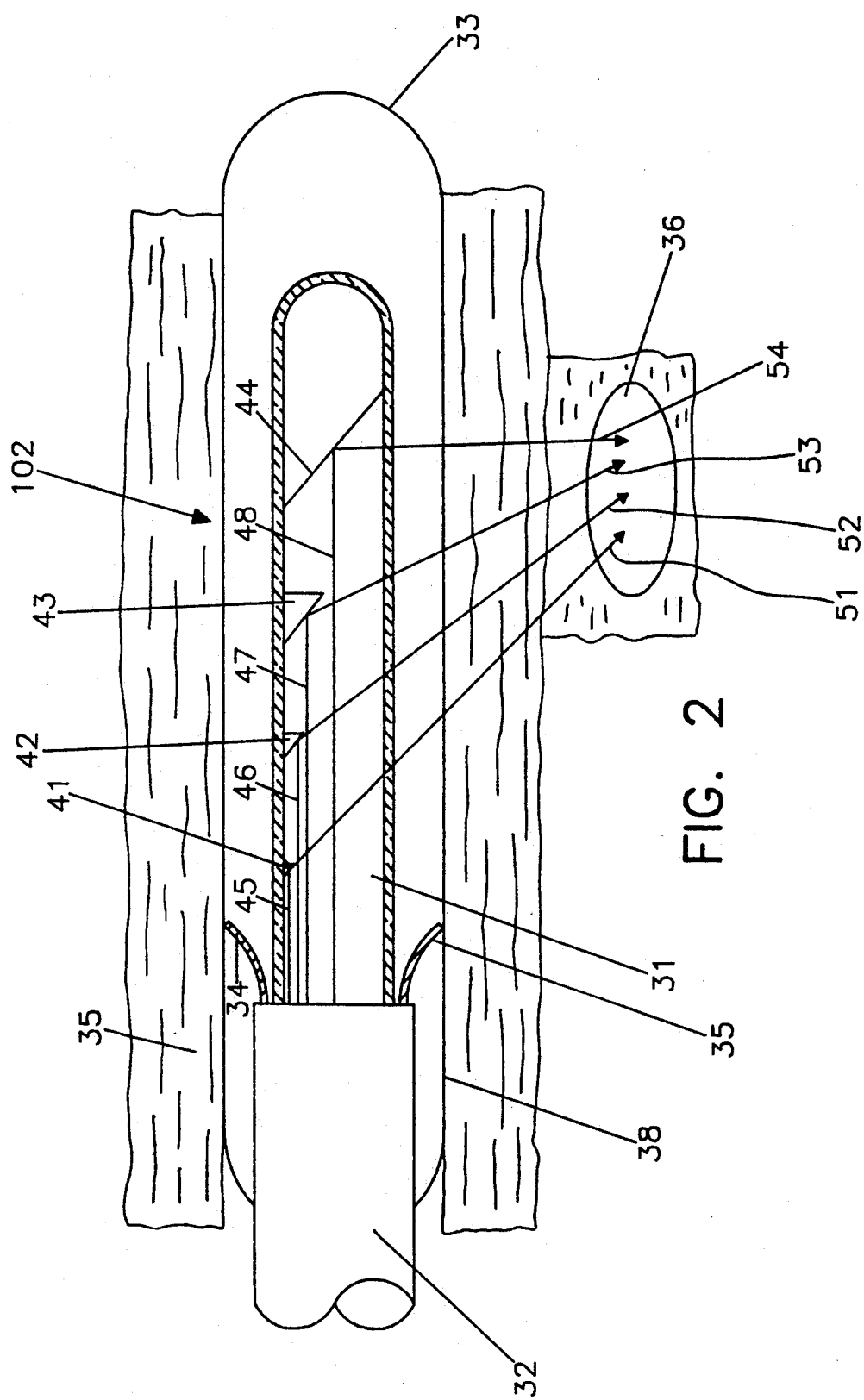
FIG. 2 shows another radial medical radiation delivery device that can be freely positioned inside a transparent, inflatable balloon incorporating temperature sensing fibers as well, placed to irradiate the prostate.

FIG. 2 now illustrates how another such device 102 is employed to shrink the prostate gland and thus provide a free passage in the urethra. As known, the prostate gland can swell and thus result in an inconvenience for a high number of men, particularly at higher age, in as much as the urethra is thus partially blocked and the free flow of urine can be obstructed. It is known that by irradiating the prostate, and thus degenerating and shrinking it this inconvenience can be removed, and a free passage restored. In order to perform this procedure in a controlled and safe manner a present invention radial medical delivery device 102 comprising an optical fiber 31, a multilumen channel 32, an inflatable balloon 33 as well as temperature sensing fibers, such as fibers 34 and 35, is introduced into the urether 35. Fiber 31 has grooves 41, 42 and 43 and cut end 44, as shown. After inflating the balloon that is transparent to the radiation wavelength used in the procedure (example, 1064 nm) radiation is directed at the prostate 36. The inclinations of the grooves 41, 42 and 43 and cut tip 44, vary in this example, so that the radiation represented incoming by arrows 45, 46, 47 and 48, and outgoing by arrows 51, 52, 53 and 54, converges toward the prostate 36.

The radiation is thus effectively penetrating the urether wall 38 in a less concentrated form than it is hitting the prostate, thus limiting the damage done to it.

The balloon 33 can be cooled by gas or liquid to further protect the prostate wall. By feeding the temperature reading obtained via sensing fibers 34 and 35 back to a laser power control, an optimum radiation level can be obtained.

In this example of a preferred embodiment of the radial medical delivery device, the grooves 41, 42, 43 and the cut tip 44 of the distal end 50 of the fiber, shown in part in FIG. 3 are at least partially covered by a reflective metal 57, 58 and 59 (such as gold) to deflect the radiation. Dark areas 61, 62 and 63, for example, receive substantially no radiation.

FIG. 4 shows a cross section and illustrates how, by flattening the lower side 60 of the fiber 31 focusing in all but the desired dimension and direction may be avoided.

The superiority over the present state of the art will now be clear: Compared to a single reflective (or totally reflective) point source on the end of a fiber the energy density penetrating through the balloon and the urether wall is much lower and a certain degree of focusing can be achieved, if desired, towards the prostate.

FIG. 5 shows prior art systems 103 with typical scattering cap 71 employing a glue 74 mixed with scattering particles 72. The radiation from fiber 70 scatters randomly and has no predetermined area of application.

The present invention device is much better directed, more power can be handled, and more successful surgeries can be accomplished. For example, with the FIG. 5 prior art system 103, radiation in direction 73 might damage the sphinxtor muscle in a prostate irradiation case. The controlled directed irradiation utilizing the present invention device will avoid such likelihoods.

Referring now back to FIGS. 2 tnrough 4 of the present invention for prostate degeneration, a fiber of synthetic silica could be used to deliver the laser power at 1064 nm. The fiber for sensing the tissue temperature may be of silver halide semi-crystalline material (transmitting a wavelength range between 4 um and 16 um). In this case, the cladding on the core may be air.

Any other available or known materials may be used for the fiber for a particular application without exceeding the scope of the present invention. For example, it can be equally possible to make the radial medical radiation delivery device employing a silver halide fiber for the laser delivery itself.

In this case a CO or CO2 laser can be used as a radiation source with wavelength of around 5 um and typically 10.6 um. In this case, the same fiber through which the laser radiation passes for irradiating the tissue can also be used to measure tissue temperature as well, as illustrated in FIG. 6 and FIG. 7.

Figure 6:
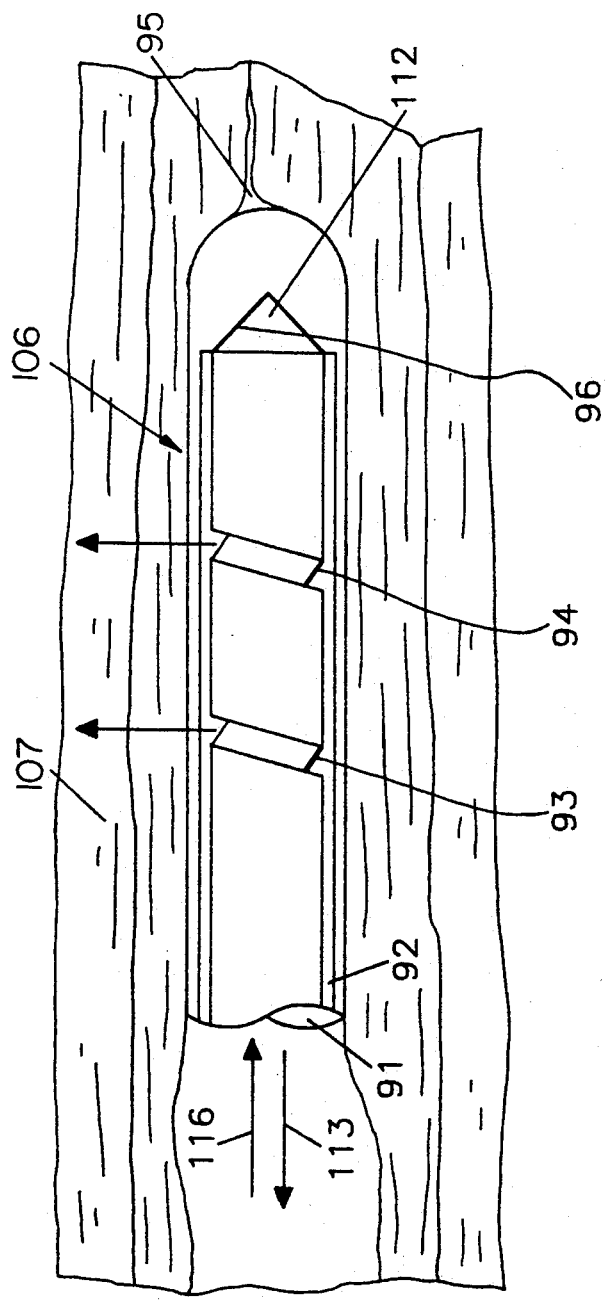
FIG. 6 shows a delivery device with spiral grooves.
Figure 7:
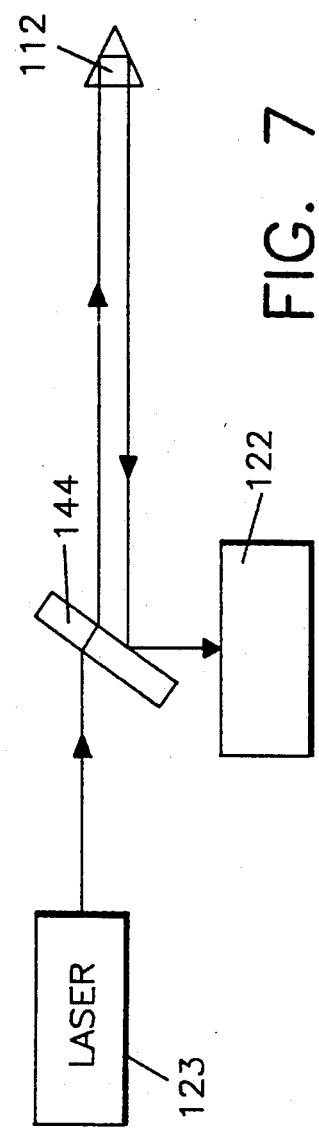
FIG. 7 shows a power control system operated by sensing through the same fiber.

FIG. 6 shows present invention device 106 a silver halide fiber consisting of core 91 and clad 92. In this case, circular cut angled grooves 93 and 94 and tip 96, as well as a transparent cap 95 are included. While the laser radiation 116 is targeted towards the tissue 107, the temperature radiation from tissue 108 is picked up by the fiber and transmitted via a reflector 112 formed at tip 96, in the optical path of the transmission, and fed back as shown by arrow. As shown in FIG. 7, this feedback is diverted via prism 114 towards a laser control module 122 thus controlling the power output of the laser 123 in line with procedural requirements.

It is evident that in some instances it may be preferable from a manufacturing standpoint to fuse a tip of a fiber containing the grooves on to another fiber, thus effectively in the end obtaining a device similar in operative characteristics to the ones described so far, and the present invention device may include a fiber formed of such joined sections without exceeding the scope of the present invention.

Clearly, in some instances it may be advantageous to build the delivery system of more than one delivery fiber processing the characteristic as described so far in this invention, for instance in order to provide higher flexibility of the device while still maintaining a certain total cross section, a fiber bundle may be used, without exceeding the scope of the present invention. Such bundles may have fibers with identical configurations but slightly staggered to enhance transmission, or may form components of a single desired configuration, depending upon the application(s) intended.

Obviously, numerous modifications and variations of the present invention are possible in light of the above teachings. It is therefore understood that within the scope of the appended claims, the invention may be practiced otherwise than as specifically described herein.

What is claimed is:

1. A medical delivery system capable of emitting radiation with wavelengths between 190 nm and 16 um in one or more essentially directed, predetermined patterns, which comprises:

(a) at least one solid optical fiber, having a core and a cladding on said core and said cladding having refractive index smaller than the core, having an input end suitably configured to connect to an appropriate radiation source and having a distal end in the proximity of which two or more grooves are penetrating into the core, said grooves having at least partial reflector capability so as to deflect radiation in one or more predetermined patterns; and, (b) a cap placed over said at least one fiber at its distal end and over said two or more grooves.

2. A radial delivery system as claimed in claim 1, further characterized by filling the grooves with a material having significantly lower reflective index than the fiber core.

3. A medical radiation delivery system as claimed in claim 1, wherein said at least one solid optical fiber transmits radiation at wavelengths between 190 and 3000 nm.

4. A medical radiation delivery system as claimed in claim 1, wherein said at least one solid, fiber is a silver halide fiber which transmits radiation at wavelengths between 4 um and 16 um.

5. A medical radiation delivery system as claimed in claim 1, wherein said grooves are only on one side of said at least one solid optical fiber.

6. A medical radiation delivery system as claimed in claim 1, wherein said grooves have inclinations which vary in said at least one solid optical fiber so as to give a radiation pattern converging at a predetermined distance from the fiber axis.

7. A medical radiation delivery device system as claimed in claim 1, wherein said at least one solid optical fiber has a distal end which is located within an inflatable balloon in a movable manner, said inflatable balloon having a cylindrical portion, and being transparent at least over its cylindrical portion to the radiation wavelength used.

8. A method of performing a laser prostatectomy procedure, comprising:

(a) the inserting of a cystoscope into the urethra;

(b) positioning a device within said cystoscope, which device includes at least one solid optical fiber, having a core and having a cladding on said core and said cladding having a reflective index smaller than the reflective index of the core, having an input end suitably configured to connect to an appropriate radiation source and having a distal end in the proximity of which two or more grooves are penetrating into the core, said grooves having at least partial reflector capability so as to deflect radiation thereto radially in one or more predetermined patterns; and having a cap placed over said fiber at its distal end and over said two or more grooves said positioning of said device being such that at least said distal end said cap are positive into the urethra; and, (c) irradiating the prostate area to be degenerated.

9. The method of claim 8 wherein said device is further characterized by said grooves having been filled with a material having significantly lower reflective index than the reflective index of the fiber core.

10. A method of performing photodynamic therapy, comprising:

(a) applying a photosensitive substance to an area to be treated or to a distal end of the device set forth below;

(b) inserting a device which includes at least one solid optical fiber, having a core and a cladding on said core and said cladding having refractive index smaller than the core, having an input end suitably configured to connect to an appropriate radiation source and having a distal end in the proximity of which two or more grooves are penetrating into the core, said grooves having at least partial reflector capability so as to deflect radiation thereto radially in one or more predetermined patterns, and a cap being placed over said at least one fiber at its distal end and over said two or more grooves; and, (c) irradiating the tissue to a predetermined dosage level.

11. The method of claim 10, wherein said device is further characterized by said grooves having been filled with a material having significantly lower reflective index than the reflective index of the fiber core.

* * * * *